(12) United States Patent
Seip et al.

(10) Patent No.: US 9,272,231 B2
(45) Date of Patent: Mar. 1, 2016

(54) HEAT EXCHANGE IN FLUID DEGASSING

(75) Inventors: Ralf Seip, Carmel, NY (US); Evgeniy Leyvi, Riverdale, NY (US); Jose Manuel Inocencio Azevedo, Mahopac, NY (US)

(73) Assignee: KONINKLIJKE PHLIPS N.V., Eindhoven (NL)

( * ) Notice: Subject to any disclaimer, the term of this patent is extended or adjusted under 35 U.S.C. 154(b) by 55 days.

(21) Appl. No.: 14/239,289

(22) PCT Filed: Sep. 4, 2012

(86) PCT No.: PCT/IB2012/054558
§ 371 (c)(1),
(2), (4) Date: Feb. 18, 2014

(87) PCT Pub. No.: WO2013/035035
PCT Pub. Date: Mar. 14, 2013

(65) Prior Publication Data
US 2014/0196607 A1    Jul. 17, 2014

Related U.S. Application Data

(60) Provisional application No. 61/531,411, filed on Sep. 6, 2011, provisional application No. 61/692,015, filed on Aug. 22, 2012.

(51) Int. Cl.
*B01D 19/00* (2006.01)
*A61B 17/225* (2006.01)
*A61B 8/00* (2006.01)

(52) U.S. Cl.
CPC ............ *B01D 19/0036* (2013.01); *A61B 8/546* (2013.01); *A61B 17/2251* (2013.01)

(58) Field of Classification Search
CPC ............. A61N 7/00; A61N 7/02; A61B 8/00; A61B 2017/2253; A61B 2018/00023; A61B 2019/5276
USPC ............... 95/249; 73/620, 626; 600/109, 439, 600/440, 446, 459; 601/2–4
See application file for complete search history.

(56) References Cited

U.S. PATENT DOCUMENTS 4,231,373 A * 11/1980 Waxman et al. ............... 600/446
4,241,412 A * 12/1980 Swain ........................... 708/442

(Continued)

OTHER PUBLICATIONS

Instructions for Use; Easy Water Degasser 4510 000 81591; Detailed Specifications & Technical Data, Model SRDS-1000, Nov. 2008, pp. 1-7.

*Primary Examiner* — Duane Smith
*Assistant Examiner* — Minh-Chau Pham

(57) ABSTRACT

A device degasses fluid in a circulation loop. The device includes a degassing chamber coupled inline with the circulation loop, where a vacuum within the degassing chamber draws out dissolved gas and water vapor from the fluid. The degassing chamber has an opening enabling gas and water vapor drawn out from the fluid, and condensation formed from the water vapor, to flow out as a result of gravitational pull. The device further includes a cooler coupled to the opening in the degassing chamber and a water trap coupled to the cooler. The cooler includes a heat exchanger configured to condense a remaining portion of the water vapor into liquid, where the condensation and liquid accumulate in the water trap. The degassing chamber, water trap and cooler are maintained under vacuum, where the degassing chamber is maintained under vacuum through the opening via the cooler and the water trap.

16 Claims, 1 Drawing Sheet

(56) References Cited

U.S. PATENT DOCUMENTS

| | | | |
|---|---|---|---|
| 4,248,090 A * | 2/1981 | Glenn | 73/620 |
| 4,257,271 A * | 3/1981 | Glenn | 73/626 |
| 4,274,422 A * | 6/1981 | Anderson et al. | 600/440 |
| 4,290,310 A * | 9/1981 | Anderson | 73/626 |
| 4,317,370 A * | 3/1982 | Glenn | 73/620 |
| 4,324,258 A * | 4/1982 | Huebscher et al. | 600/455 |
| 4,325,381 A * | 4/1982 | Glenn | 600/446 |
| 4,327,738 A * | 5/1982 | Green et al. | 600/109 |
| 5,195,509 A | 3/1993 | Rentschler et al. | |
| 6,685,639 B1 | 2/2004 | Wang et al. | |
| 7,559,905 B2 * | 7/2009 | Kagosaki et al. | 601/3 |
| 2005/0154309 A1* | 7/2005 | Etchells et al. | 600/459 |
| 2011/0072970 A1* | 3/2011 | Slobodzian et al. | 95/249 |

* cited by examiner

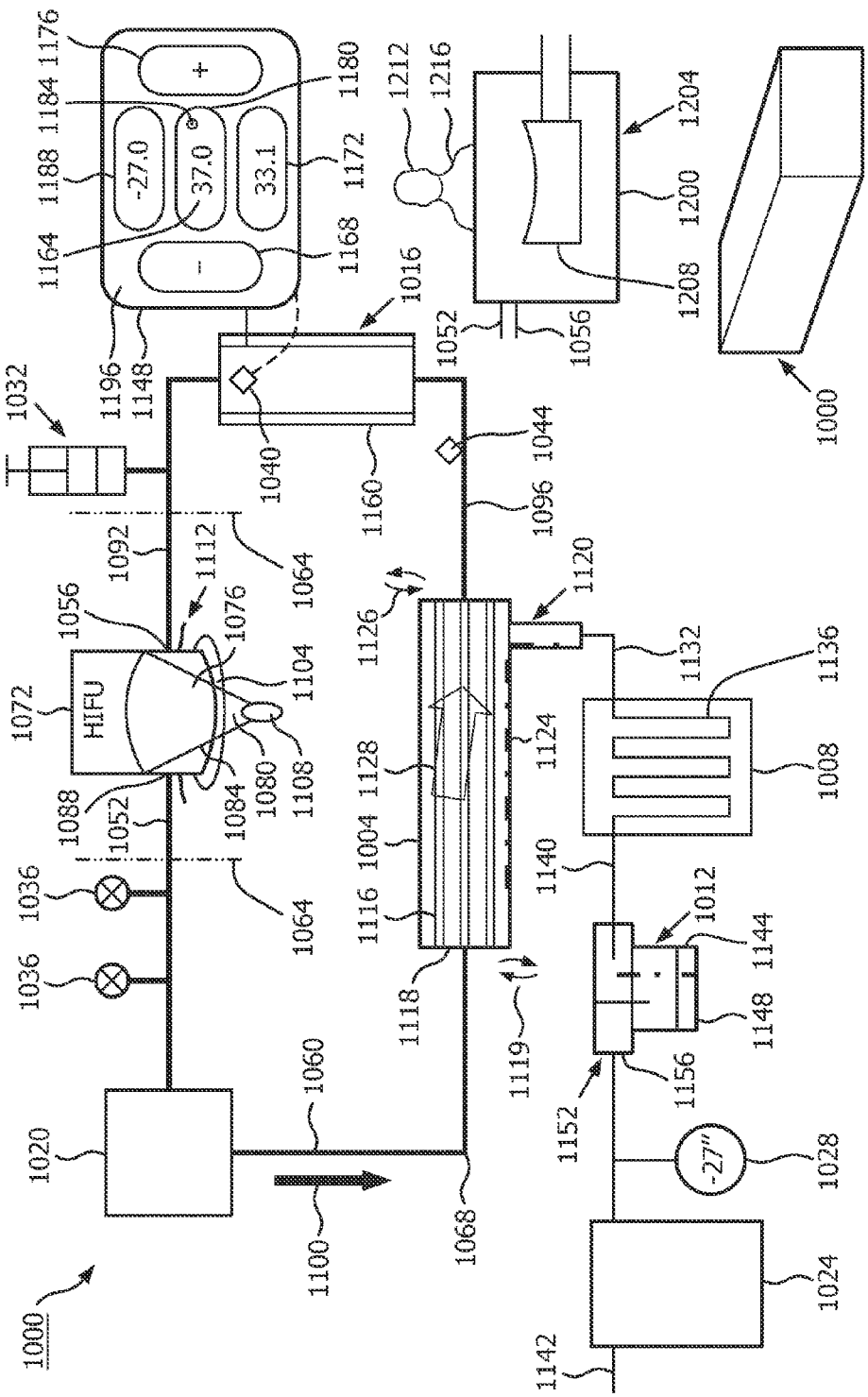

HEAT EXCHANGE IN FLUID DEGASSING

This application is the U.S. National Phase application under 35 U.S.C. §371 of International Application No. PCT/US2012/054558 filed Sep. 4, 2012 which claims the benefit of U.S. Provisional Patent Application No. 61/531,411 filed Sep. 6, 2011 and U.S. Provisional Patent Application No. 61/692,015 filed Aug. 22, 2012. These applications are hereby incorporated by reference herein.

FIELD OF THE INVENTION

The present invention relates to degassing a fluid and, more particularly, to a degassing system that utilizes heat exchange.

BACKGROUND OF THE INVENTION

A liquid of low viscosity is required to couple high-intensity focused ultrasound (HIFU) transducers to the targeted tissue/organ, e.g., the abdomen, in both clinical and pre-clinical applications. A second, very thin layer of coupling medium, e.g., a gel, intervenes for direct contact with the skin of the patient.

The liquid, such as water, should be relatively pure, with a dissolved oxygen content less than or equal to three parts per million (PPM). Otherwise, the high-intensity focused field can easily create cavitation bubbles in the coupling fluid that could block and/or distort the ultrasound field. Inefficiencies in HIFU transducers are mainly in the form of heat they locally generate. The heat is continuously removed by the liquid coupling medium flowing laterally along and past the face, i.e., ultrasound interface surface, of the transducer.

Degassed water is also routinely used in the ultrasound transducer industry during transducer quality control and calibration procedures.

In one degassing method, the fluid passes degassed through a tube made of a semi-permeable material that allows only gases to permeate through the membrane, but not liquids. This is due to the tube's internal hydrophobic (i.e., water-repelling) coating. A vacuum is applied around the outer surface of the tube. The resulting pressure gradient draws the dissolved gasses out of solution. An example of this is found in U.S. Patent Publication No. 2005/0154309 to Etchells et al. (hereinafter "the Etchels publication"), the entire disclosure of which is incorporated herein by reference. Since the degassing chamber is in the shape of a tube, it lends itself nicely to closed-loop (i.e., inline) operation.

In another method, the fluid in a closed container is subjected to a vacuum. The vacuum lowers the boiling temperature, to remove (i.e., boil away) the dissolved gases of the fluid. As the fluid needs to be in the closed container under vacuum for some time, this approach does not lend itself to closed-loop/inline operation. Instead, these degassers will typically work in "batch" mode, wherein a certain amount of water will be ready for use after having been degassed for some time. A lot of user interaction is generally required to generate the degassed water, retain it, and transfer it to its final application.

Both approaches are able to degas water to a dissolved oxygen content less than or equal to one PPM quite easily, provided that the vacuum applied to either the outside of the semi-permeable tube (in the case of the hollow-filter cartridge) or to the closed container (in the case of batch degassers) is high. Typically, a pressure of between −27 and −29 inches of mercury (Hg) is required.

SUMMARY OF THE INVENTION

On the one hand, the colder the coupling medium, the more efficiently it removes heat from the HIFU transducer; however, both of the above-described approaches fail to properly degas the water when its temperature is raised above room temperature.

For pre-clinical research, it is advantageous to maintain the temperature of the degassed water (which is in contact with the animal) at the animal's body temperature. Otherwise, the animal (whose sizes can sometimes be comparable to the larger size of the coupling water bolus) is exposed to unnecessary stress and discomfort, as it tries to up-regulate its metabolism to compensate for its body's heat loss to the (colder) coupling fluid. This is especially difficult for the animal, which is typically under anesthesia during these procedures, which further hampers its ability to regulate body temperature properly, potentially yielding incorrect experimental conditions and results, especially in pre-clinical experiments that rely on normal blood-flow conditions (i.e., drug delivery experiments). Small animals (i.e., mice, rats) are particularly at risk of hypothermia, since many of the ultrasound applicators used for pre-clinical research are large with respect to the animal, and can quite effectively act as a heat sink.

In clinical applications (i.e., using extracorporeal HIFU applicators coupled to the patients skin via a coupling bolus containing degassed water), heat loss from the patient is not as large of an issue as it is in the case of small-animal research, but comfort can be increased by temperature-controlling the coupling water bath temperature. Also, since HIFU transducers are typically not 100% efficient, there is a steady warming of the coupling water during a treatment. While possibly comfortable to the patient, too much warming can cause skin burns and also degrades HIFU ultrasound transducer performance. Thus, active temperature regulation of the coupling fluid is also required for these purposes: transducer cooling, and minimizing unnecessary patient skin burns/skin overheating, all the while maintaining an acceptable level of dissolved gases (i.e., ≤3 ppm or ≤3 mg/L) to prevent cavitation bubbles from forming.

What is needed is a system that is able to degas the coupling fluid, control its temperature, and operate in a closed-loop/inline manner.

As noted above, both of the approaches described in the "Background of the Invention" section of this patent application fail to properly degas the water when its temperature is raised above room temperature.

More specifically, warm water generates water vapor more easily, and so does a vacuum.

By itself, this would not be a problem. Within a degassing system, however, where warm water is being generated (i.e., by a heating element or heat exchanger) and degassed at the same time, certain practical problems prevent proper degassing system operation.

For systems based on the hollow-filter cartridge, the present inventors have observed that the state-of-the-art industry has still been unable to devise hydrophobic coatings or membrane materials on the inside of the tubes that allow gases to permeate out of the water flowing through the tube while preventing both the water and the water vapor from permeating across the tube. In particular, current coatings or membrane materials allow the gases to permeate across them, prevent the water from permeating across them, but also allow the water vapor to permeate across them. As such, water vapor accumulates in the vacuum created around the hollow tubes, condenses, accumulates more, and eventually reaches the vacuum pump. The performance of vacuum pumps degrades significantly when pumping water vapor (rather than air), and degrades catastrophically when trying to pump liquids, as would be the case after some time when enough water vapor has permeated across the membrane, condensed on the other side and reached the vacuum pump.

In systems based on the batch degasser vacuum chamber, the same occurs. Significantly larger amounts of water vapor are generated by the warm water being degassed. The vapor condenses on the vacuum pump mechanism. This reduces the vacuum level (and thus reduces the ability of the system to degas the warm water properly), finally rendering the degassing system inoperable.

In short, at higher than room temperature, existing cartridges/filters become saturated with water vapor, leading to condensation and device flooding. This compromises their ability to operate correctly.

In some cases, it is possible to degas and warm water to a desired level, and then transfer this water to an appropriate ultrasound transducer coupling bolus to provide warm coupling to a target region for some limited amount of time (before, for example, the water cools down again or the water re-gases as it naturally absorbs gases from the atmosphere). Such an arrangement, however, is not convenient and is not simple to use. It also has significant implications on pre-clinical or clinical workflow that necessitates the degassed water being maintained at a particular temperature.

In other cases, it is possible to oversize the vacuum pump so as to mitigate the effect of the water vapor; however, although this may be possible for larger, stationary systems, it is not practical for smaller clinical systems or portable stand-alone systems, where space may be at a premium and noise levels may need to be minimized.

In summary, the following problems need to be solved. Water vapor tends to condense and accumulate inside the degasser filter cartridge. It also tends to condense and accumulate inside the vacuum pump used to create the vacuum required for water degassing. Finally, there exists a need for water degassing, temperature control, and closed-loop/inline operation functions to be integrated together within a single system that requires minimal operator intervention and control.

The present invention is directed to addressing one or more of the concerns discussed herein above.

Particularly, accumulation of condensed water in the degasser filter cartridge is preventable by aligning it in such a way as to allow water to flow out of it by gravity. Otherwise, the external surface of the semi-permeable tubing in the degasser filter cartridge could be completely submerged in water, preventing it from degassing any additional water.

Another measure is to actively cool the water vapor to force it to condense into water at room temperature or below as soon as it exits the degasser filter cartridge.

One further step is forcing this cold water from the cooler into a water trap the user can access for emptying it or which is automatically emptied. The water vapor, and the water formed by its condensation, therefore do not reach the next stage, the vacuum pump that vacuumizes the preceding water trap, cooler and degasser filter cartridge.

A temperature-maintenance device, in accordance with what is proposed herein, allows its easy addition to existing HIFU water management systems, while the device's temperature control capability keeps the coupling water temperature at a desired setpoint for the duration of the pre-clinical experiment. Combining degassing and temperature control into a single unit simplifies experimental setup and workflow. Finally, the degasser also provides an attractive, simple, and cost-effective alternative to currently used vacuum batch degassing and water boiling degassing methods.

The temperature-maintenance device has a heater and is, in one aspect or version, configured for placement in a circulation loop of an ultrasound transducer coupling bolus, for degassing circulating liquid of the loop and for operating the heater to perform temperature control of the liquid.

In a sub-aspect, the device is further configured for setting a fixed operating temperature, and maintaining the liquid at the operating temperature at the bolus.

In a further sub-aspect, the operating temperature is at least 21 degrees centigrade.

In a yet further sub-aspect, the operating temperature is at least 36 degrees centigrade.

In a related sub-aspect, the temperature control is configured for maintaining, at the bolus, said liquid at an operating temperature at least as high as a steady-state body temperature of a live human, or live warm-blooded animal, subject for undergoing ultrasound exposure via said bolus.

In another sub-aspect, the device includes a degassing chamber that, starting from the bolus, flow-wise precedes the heater in the loop.

In a sub-aspect, the device includes a water trap and is configured for using the trap to compensate for increased evaporation caused by applying the temperature control to heat the liquid at the above-mentioned point.

As a further sub-aspect, the device includes a cooler that precedes the water trap, and follows a degassing chamber, in a path of fluid being diverted from the loop.

In an alternative or complementary sub-aspect, the trap has an exit and, at the exit, a semi-permeable filter for allowing gas, but not liquid, to pass.

In a general sub-aspect, the device is configured for being portable room-to-room in a clinical environment.

As a particular sub-aspect, the device includes a degassing chamber aligned and configured so as to allow, during the degassing, condensation within the chamber to, automatically and without need for user intervention, flow out of the chamber as a result of gravitational pull.

In one other sub-aspect, the device includes a degassing chamber having an inlet for the liquid and a replaceable filter at the inlet.

In another version, which pertains to either inline and batch operation, a fluid degassing device includes a degassing chamber, a water trap, and an intervening cooler. The chamber, trap and cooler are all vacuumized.

As a sub-version, the device further includes a heater in a path of the fluid. The device is configured for operating the heater for performing temperature control of the fluid.

In an alternative or further developed sub-version, the fluid provides an ultrasound transducer coupling bolus.

In a further sub-version, the device is configured such that the bolus serves as a supporting platform for a subject undergoing ultrasound exposure via the bolus.

In another sub-version, the device further includes a heater and a circulation pump, and is designed compact so as to be holdable up in one hand without the need for a handle.

In one of a number of additional sub-versions, the device includes a heating element for temperature control of the fluid and, on the heating element, a sensor. The device is configured for controlling the heating element based on feedback from the sensor.

In one other of the additional sub-versions, the water trap is implemented for separating out liquid.

In yet another of the additional sub-versions, the device is configured for, automatically and without need for user intervention, emptying the water trap.

In still one other of the additional sub-versions, the fluid undergoing the degassing circulates in a closed loop to thereby re-enter, after exiting, the chamber.

In a yet, additional subversion, the chamber is configured and aligned for letting condensation automatically drain out.

In a further aspect of the subversion, the fluid is a liquid, and the chamber is configured for degassing the liquid for use as an ultrasound coupling medium. The chamber is aligned and configured so as to allow, during the degassing, the condensation to, automatically and without the need for user intervention, flow out of said chamber as a result of gravitational pull.

A computer-related embodiment features a computer readable medium for a temperature-maintenance device that comprise a heater, the device being configured for placement in a circulation loop of an ultrasound transducer coupling bolus, for degassing circulating liquid of the loop and for operating the heater to perform temperature control of the liquid. The medium embodies instructions executable by a processor for functions, among which is receiving, via a user control, a setting for the temperature control of the liquid of the loop.

Details of the novel, compact temperature-control/fluid-degassing device are set forth further below, with the aid of the following drawing, which is not drawn to scale.

BRIEF DESCRIPTION OF THE DRAWING

FIG. 1 is a schematic diagram of a compact temperature-control/fluid-degassing device in accordance with the present invention.

DETAILED DESCRIPTION OF EMBODIMENTS

FIG. 1 shows, by illustrative and non-limitative example, a temperature-control/fluid-degassing device 1000. The embodiment shown in FIG. 1 pertains particularly to an inline device, but also shows components usable in a batch device. An inline device will be discussed first.

The degassing device 1000 includes a degassing chamber (or "degassing filter cartridge") 1004. Also included are a cooler 1008 and a water trap 1012. Among the further components of the device 1000 is a heater 1016, a self-priming circulation pump 1020, a vacuum pump 1024, a vacuum gauge 1028, a water-volume-adjustment expansion tank 1032, and system fill/drain valves 1036. An additional component is an on-heater temperature sensor 1040, or alternatively an inline temperature sensor 1044. The device 1000 also includes a user interface 1048 such as a touchscreen; water inlet tubing 1052, water outlet tubing 1056; internal water transit tubing 1060; and a housing 1064. The device 1000 further includes some components not shown in FIG. 1, among which are an AC/DC power supply, a fan, and a microcontroller having a computer-readable medium.

The outlet tubing 1056 conveys circulating water 1068, here to an ultrasound transducer 1072 such as a HIFU transducer. Although HIFU is used as an example above, any type of ultrasound exposure: focused, unfocused, high intensity, low intensity, etc. is within the intended scope of what is proposed herein.

Specifically, the circulating water 1068 is delivered, as a stream that circulates throughout the device 1000. While coming into proximity of the transducer 1072, the water, such as distilled water, 1068 serves as a coupling bolus 1076 of the transducer. The coupling bolus 1076 acts as coupling medium between the transducer 1072 and a target of ultrasound 1080 to be applied to a target. The coupling bolus 1076 is contained by a flexible coupling membrane 1084 which covers and extends out from the ultrasound interfacing surface of the transducer 1072. The coupling membrane 1084 may be made out of a thin latex or silicone sheath. It has openings 1088, 1092 for connection to the tubing 1052, 1056 to afford real-time circulation of the water 1068 in a closed loop 1096. The circulation is in the direction indicated in FIG. 1 by the circulation direction arrow 1100. Particularly for medical applications, a coupling gel 1104 or other coupling medium for immediate interface with the target will be employed. The ultrasound 1080 can be focused to a transducer focal zone 1108. The fiscal zone 1108 is within the body of a live human, or live subject, such as a medical patient. Via the gel 1108, the direct connection is made with the skin 1112 of the subject. The above-specified components of the device 1000 reside within the housing 1064, except that the inlet and outlet tubing 1052, 1056 extend to protrude outside the housing, as does a cord with a wall plug, and the touchscreen 1048 and fan grille are built into or are part of respective outside walls of the housing.

The water 1068 in the portion of the internal water transit tubing 1060 from the circulation pump 1020 to the cartridge 1004 is distributed upon entry into the cartridge, as for example in the Etchells publication. The distribution occurs flow-wise among semi-permeable tubes or capillaries 1116 that run longitudinally inside and throughout the cartridge 1004. As the capillaries 1116 have a very small cross-section, a pre-filter 1118 is connected to the water inlet of the cartridge 1004, to prevent clogging of the capillaries and extend the life of the cartridge. The pre-filter 1118 is replaceable, as indicated in FIG. 1 by the arrows 1119.

The vacuum created within the cartridge 1004 draws out the dissolved gas, which is our objective, but also draws out water vapor.

The present inventors have found, as mentioned above, that a solution to the problem of water vapor condensation in the cartridge 1004 is to configure and align the cartridge to allow, during the degassing, the condensation to, automatically and without the need for user intervention, flow out of the cartridge as a result of gravitational pull. This can be done by providing an opening 1120 in the bottom of the cartridge 1004. The cartridge 1004 is aligned so that condensation 1124 flows out the opening 1120. An arrow in FIG. 1 shows the direction of flow 1128 toward the opening 1120. As seen from the arrow pair 1126, the cartridge 1004 is replaceable.

The tubes 1116 are thereby prevented from being submerged which would render them ineffective in degassing any additional circulating water 1068.

However, the vacuum maintained within the cartridge 1004 must be imposed from outside by means of the continuously-open opening 1120, i.e., the opening through which the condensed water vapor exits.

There accordingly still exists the problem, which this proposal likewise addresses, of how to keep the condensation 1124, and exiting water vapor, from reaching the vacuum pump 1024.

As an intermediate step, an inlet 1132 to the cooler 1008 receives the water and water vapor, to condense the remaining vapor into water at room temperature or below. The cooler 1008 is vacuumized by its indirect connection to the vacuum pump 1024. The cooler 1008 can be constructed using a Peltier junction, heat exchanger or equivalent apparatus. A network of tubes 1136 can be used to maximize surface area contact with the cold side of the Peltier junction. The tubes 1136 are narrow to maximize inner-surface contact with their fluid content. Their diameters are made small enough so as to separate the water vapor region of the system from the vacuum pump 1024.

The output of the cooler 1008, i.e., water and possibly some remaining water vapor, is received at an inlet 1140 to the water trap 1012 which is directly vacuumized by the vacuum pump 1024 which has an air exhaust 1142. Water accumulates in a pool 1144 at the bottom of the water trap 1012. The water trap 1012 is sized large enough to allow uninterrupted operation of the device 1000 for the duration of the experiment or pre-clinical research procedure, or of the clinical procedure. Thus, user intervention is minimized and workflow is streamlined.

The device 1000 may include a motorized trap emptier 1148 that can operate on feedback from its sensor within the water trap 1012 that indicates a "water trap full" condition. A floating element could, for instance, break the line of sight to an infrared receiver. The emptier 1148 has a motorized assembly that automatically, and without the need for user intervention, opens, drains, and re-seals the trap. This occurs while automatically placing the device 1000 otherwise "on hold" during this time. The water can drain into a sink drain, for example, alleviating the need for any user intervention for a relatively long period of time. In one embodiment, the motor unscrews an annular part of the bottom of the trap 1012, pulling it out of engagement, and reverses the process to seal up the trap. In another embodiment, the water trap 1012 has a valve that is opened automatically, and without the need for user intervention, which allows the water trap to drain. Then, the valve is closed, re-sealing the trap. Alternatively, a user-actuatable apparatus 1148 for emptying the trap 1012 can consist of a bottom transparent cup of the trap that can be unscrewed for removal. The trap 1012 is to be emptied by the user at regular intervals, such as every two to three hours during operation of the device 1000. In either embodiment, the trap 1012 has, at its exit 1152, a semi-permeable filter 1156 for allowing gas, but not liquid, to pass. The motorized embodiment may also empty the trap 1012 periodically, and is therefore implementable without the water-trap-full sensor.

The vacuum gauge 1028, which is here electrical but may be mechanical, further adds to the reliability of the system. Achieving a desired dissolved gas level entails providing a sufficiently robust vacuum level, such as −27" Hg (inches of mercury).

The microcontroller (not shown) is connected to the vacuum gauge 1028, the on-heater temperature sensor 1040, the motorized trap emptier 1148, and the touchscreen 1048.

Degradation in the vacuum is usable as a failure detection mechanism. In particular, accumulated water inside the sensor of the gauge 1028 would indicate malfunction of the cooler 1008, or that it is time for the user to empty the water trap 1012. During operation, the vacuum should measure between −24" and −29" Hg.

The on-heater temperature sensor 1040 resides on a heating element 1160 of the heater 1016 and can be realized as a thermocouple or thermistor for example. The microcontroller controls the heating element 1160 based on feedback from the sensor 1040. If the measured temperature is lower than the desired temperature, the microcontroller turns the heating element ON; if the measured temperature is higher, the microcontroller turns the heating element OFF. By locating the temperature sensor 1040 on the heating element 1160 itself, additional reliability can be achieved, as overheating of the system or components can be prevented if, for example, the circulation pump 1020 were to fail. Locating the temperature sensor 1040 inline would not detect this fault, as the water 1068 would not be circulating, and would never bring warmer water across the sensor. Alternatively or in addition, the device 1000 may be implemented with the inline temperature sensor 1044 which measures the temperature of the water 1068. As another alternative, a thermostat can be directly connected to the sensor(s) 1040, 1044. FIG. 1 depicts the cartridge 1004 as, starting from the bolus 1076, flow-wise preceding the heater 1016 in the loop 1096. By having the cartridge 1004 precede the heater 1016, heat loss of the water 1068 as it traverses through the cartridge is minimized. Thus, the duty cycle of the heater 1016 is eased. Further, the temperature of the water 1068 that flows through the cartridge 1004 is lower than it would otherwise be. This reduces the amount of water vapor drawn out in the cartridge 1004. Accordingly, there is less condensate to prevent from reaching the vacuum pump 1024. As a result, the user water trap emptying frequency is lowered, and higher bolus temperatures can be accommodated without running up against limits of the device 1000 as implemented. Overall, placing the heater 1016 after the cartridge 1004 yields a better performing system. Alternatively, the heater can instead be placed earlier in the loop so to precede the cartridge.

A fixed operating temperature (or "setpoint") 1164 is enterable by the user on the touchscreen 1048 which is connected to the microcontroller.

The indicator 1184 cycles on as the circulating water 1068 is being heated to the entered setpoint 1164 and off when the setpoint is attained. At this point, subsequent cooling from the degassing chamber 1004 and the ambient environment causes the heater 1016 and thus the indicator 1184 to cycle on once again. In this manner, the temperature of the circulating water 1068, as measured at the sensor 1040, 1044, is maintained at the setpoint 1164. Due to the circulation of the water 1068, the setpoint 1164 is likewise maintained at the bolus 1076.

A decrement key 1168, and an increment key 1176, for the setpoint 1164 are provided. On the setpoint display panel 1180, there is a heater-active indicator 1184 which remains red while the heater 1016 is active. A measured vacuum reading 1188 and a current reading 1192 of the temperature sensor 1040, 1044 are displayed onscreen. Surrounding the buttons and reading panels is a background 1196 of the touchscreen 1048 that ordinarily appears blue, but turns red to alert the user. A red background color indicates that it is time to empty the water trap. For example, the red color appears after approximately 2.5 hours of continuous operation of the device 1000.

Since water escapes as water vapor through the cartridge 1004, the changing volume of water 1068 in the closed loop 1096 is accommodated. This is implementable by means of the water-volume-adjustment expansion tank 1032 and the system fill/drain valves 1036. The expansion tank 1032 contains "extra" water to introduce into the closed loop 1096 as water 1068 leaves in the form of water vapor. Or, some other means of replenishment may be utilized. (i.e., a syringe partially filled with water that is under user control). A syringe or expansion tank affords a means for relieving pressure to thereby prevent the capillaries 1116 from bursting. If this is not done, the changing water volume in the closed-loop device 1000 could change the water volume in the bolus 1076 of the transducer 1072 (which is covered with the flexible coupling membrane 1084 for good transducer assembly/patient interface). Such a change could negatively affect the transducer/bolus/target coupling interface, leading to changes of ultrasound energy being delivered as well as changes to the location of the focal zone 1108 (so that it is no longer being positioned in the intended targeted region). Luer-type locks or couplers can be applied to the water inlet, and water outlet, tubing 1052, 1056 for quickly disconnecting the transducer 1072 and for filling the bolus 1076 or water 1068.

A flow rate of 0.1 L/min (liters per minute) is provided. One liter of water at 7-8 PPM initial dissolved oxygen content can be degassed to a dissolved oxygen content less than or equal to 1 PPM in 20 minutes. The unit 1000, without its connections and built in interfaces, is shown in the lower right corner of FIG. 1. It is compact, standalone and self-contained, portable from room to room in a clinical environment. It can, in fact, be held up with one hand without the need for a handle. It has a weight of 2.7 kilograms (kg), which includes the hollow stand needed to accommodate the water trap 1012 mounted underneath. Its dimensions, which include the stand, are, in centimeters (cm), 16×25×15, in terms of width, depth and height, respectively.

A bolus 1200, to which the device 1000 is attached, can alternatively be implemented as a supporting platform 1204. The bolus 1200, as shown in FIG. 1, may surround an ultrasound transducer 1208. A small animal 1212, such a mouse or rat, can be placed on the platform 1204, its skin coupled to the bolus 1200 by coupling gel 1216. The platform 1024 can be dimensioned, for this purpose, so as to provide a top supporting surface that is a square 15 to 20 centimeters per side, for example. The water inlet, and water outlet, tubing 1052, 1056 are connected to the bolus 1200 to close the loop 1096.

The device 1000 is configured to provide physiologically important or physiologically comfortable water temperatures to the human, or animal, subject 1112, 1212. It is configured to accommodate a setpoint temperature 1164 at least as high as a steady-state body temperature of a live human, or live warm-blooded animal, subject for undergoing ultrasound via the bolus 1076, 1200. In particular, a setpoint 1164 of 37° C. (degrees centigrade) is handled by device 1000. If a lower setpoint 1164 is desired, 36° C. or a room-temperature setpoint of approximately 21 or 22° C. for example, the device 1000 will refrain from heating the water 1068 beyond the setpoint and will maintain the water at the setpoint temperature. In fact, the device 1000 can heat the supplied water up to as much as 40° C., in accordance with the setpoint 1164 entered, although the temperature limit can potentially be made higher depending on the implementation.

It is within the intended scope of what is proposed herein that the device 1000 optionally include within the loop 1096 a chiller for down-regulating the temperature of the circulating water 1068, for instance below room temperature. Such a chiller can also be implemented in addition to the heater 1016, so as to quickly alleviate a condition in which the water temperature is too high for proper operation or too high for subject comfort or safety.

The device 1000 can alternatively degas water in batch mode. The water inlet, and water outlet, tubing 1052, 1056 are placed in, for instance, a container of water to be degassed. The vacuum pump is afforded protection from water and vapor by virtue of the cooler 1008, water trap 1012, and either a batch degasser vacuum chamber aligned and configured in accordance with the principles applied herein to the degassing chamber 1004, or the chamber 1004 itself.

In one variation, a temperature-maintenance device includes a heater and is placeable in a circulation loop of an ultrasound transducer coupling bolus, for degassing circulating liquid of the loop and for operating the heater for performing temperature control of the liquid. A temperature setpoint, such as a normal body temperature, for the liquid at the bolus may be entered. A device, either open- or closed-looped with respect to fluid flow, may include, in some variations, a degassing chamber, a water trap, and an intervening cooler, all vacuumized by a vacuum pump. The chamber may be configured and aligned for letting condensation automatically drain out. The water trap may be emptied, automatically and without the need for user intervention, by a motorized trap emptier and/or be emptiable by the user.

While the invention has been illustrated and described in detail in the drawing and foregoing description, such illustration and description are to be considered illustrative or exemplary and not restrictive; the invention is not limited to the disclosed embodiments.

For example, "T" connectors and valves may be supplied to the device 1000.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A device for degassing a fluid in a circulation loop, comprising:
    a degassing chamber having an inlet and an outlet coupled inline with the circulation loop, wherein a vacuum draws out dissolved gas and water vapor from the fluid circulating in the circulation loop, the degassing chamber further having an opening, wherein the degassing chamber is configured and aligned to allow, during degassing, gas and water vapor drawn out from the fluid, and condensation formed from a portion of the water vapor drawn out from the fluid, to flow out of the degassing chamber via the opening as a result of gravitational pull;
    a cooler coupled to the opening in the degassing chamber; and
    a water-trap coupled to the cooler, such that the cooler is coupled in-between the opening in the degassing chamber and the water trap, wherein the cooler comprises a heat exchanger configured to condense a remaining portion of the water vapor drawn out from the fluid into liquid,
    said degassing chamber, said water trap and said cooler all being maintained under vacuum, wherein the degassing chamber is maintained under vacuum from outside the degassing chamber through the opening via the cooler, the cooler being indirectly coupled to a vacuum pump through the water trap, and the water trap being directly coupled to the vacuum pump, wherein the condensation and liquid accumulate in the water trap.

2. The device of claim 1, further comprising a temperature-maintenance device, wherein the temperature-maintenance device comprises a heater configured for placement in the circulation loop, wherein the circulation loop includes an ultrasound transducer coupling bolus, and wherein an operation of said heater is configured for performing temperature control of said fluid.

3. The device of claim 2, further comprising a user interface for setting a fixed operating temperature, and wherein said performing temperature control is further for maintaining said liquid at said fixed operating temperature at said ultrasound transducer coupling bolus.

4. The device of claim 2, wherein said degassing chamber, starting from said ultrasound transducer coupling bolus, flow-wise precedes said heater in said circulation loop.

5. The device of claim 2, wherein said water trap is further configured to compensate for increased evaporation caused by performing temperature control to heat said fluid.

6. The device of claim 2, further comprising a replaceable filter at said inlet of said degassing chamber.

7. The device of claim 1, further comprising a heater coupled inline with the circulation loop of said fluid, wherein an operation of said heater is configured for performing temperature control of said fluid.

8. The device of claim 1, further wherein said fluid in the circulation loop provides an ultrasound transducer coupling bolus.

9. The device of claim 8, further wherein the ultrasound transducer bolus serves as a supporting platform for a subject undergoing ultrasound exposure via said ultrasound transducer bolus.

10. The device of claim 1, further comprising a circulation pump for circulating the fluid in the circulation loop.

11. The device of claim 1, further comprising a heating element coupled inline with the circulation loop for temperature control of said fluid; and a sensor disposed on said heating element, wherein a control of said heating element is based on feedback from said sensor.

12. he device of claim 1, wherein said water trap is configured for separating out liquid.

13. The device of claim 1, further comprising a motorized assembly configured for, automatically and without need for user intervention, emptying said water trap of accumulated condensation and liquid.

14. The device of claim 1, wherein said fluid comprises a liquid, and further wherein said chamber is configured for degassing said liquid for use as an ultrasound coupling medium.

15. The device of claim 1, further comprising:
a temperature-maintenance device including a heater configured to perform temperature control of the fluid in the circulation loop; and
a user interface configured to receive a temperature setting from a user, and to provide the temperature setting to the temperature-maintenance device to perform the temperature control.

16. A device for degassing a fluid in a circulation loop, the device comprising:
a degassing chamber configured to receive the fluid circulating in the circulation loop, and to draw out dissolved gas and water vapor from the fluid circulating, the degassing chamber having an opening through which water vapor drawn out from the fluid, during degassing, flows out of the degassing chamber by gravity;
a cooler coupled to the opening in the degassing chamber to receive the water vapor, the cooler being configured to condense the received water vapor into water at room temperature or below; and
a water-trap coupled to the cooler to receive and accumulate the water from the cooler,
wherein the degassing chamber, the cooler and the water trap are all maintained under vacuum, wherein the degassing chamber is maintained under the vacuum through the opening via the cooler, which is indirectly coupled to a vacuum pump through the water trap.

* * * * *